United States Patent
Wiesel

(10) Patent No.: US 9,681,819 B2
(45) Date of Patent: Jun. 20, 2017

(54) METHOD AND APPARATUS FOR DETECTING ATRIAL FIBRILLATION

(71) Applicant: Joseph Wiesel, West Hempstead, NY (US)

(72) Inventor: Joseph Wiesel, West Hempstead, NY (US)

( * ) Notice: Subject to any disclaimer, the term of this patent is extended or adjusted under 35 U.S.C. 154(b) by 186 days.

(21) Appl. No.: 14/469,023

(22) Filed: Aug. 26, 2014

(65) Prior Publication Data

US 2015/0065891 A1 Mar. 5, 2015

Related U.S. Application Data

(60) Provisional application No. 61/871,906, filed on Aug. 30, 2013.

(51) Int. Cl.
| | |
|---|---|
| *A61B 5/04* | (2006.01) |
| *A61B 5/046* | (2006.01) |
| *A61B 5/0456* | (2006.01) |
| *A61B 5/024* | (2006.01) |
| *A61B 5/11* | (2006.01) |

(52) U.S. Cl.
CPC .............. *A61B 5/046* (2013.01); *A61B 5/024* (2013.01); *A61B 5/02438* (2013.01); *A61B 5/0456* (2013.01); *A61B 5/11* (2013.01); *A61B 2562/0219* (2013.01)

(58) Field of Classification Search
CPC ......... A61B 5/046; A61B 5/0468; A61B 5/02; A61B 5/0535
See application file for complete search history.

(56) References Cited

U.S. PATENT DOCUMENTS

| 4,260,951 A | 4/1981 | Lewyn |
|---|---|---|
| 4,685,464 A | 8/1987 | Goldberger et al. |
| 4,700,708 A | 10/1987 | New, Jr. et al. |
| | (Continued) | |

OTHER PUBLICATIONS

Joseph Wiesel et al "The Use of a Modified Sphygmonanometer to Detect Atrial Fibrillation in Outpatients", PACE, vol. 27 (May 2004).

(Continued)

*Primary Examiner* — Christopher D Koharski
*Assistant Examiner* — Natasha Patel

(57) ABSTRACT

Method of determining atrial fibrillation including determining if a patient's pulse beats form an irregular pattern and only if so, indicating the presence of an irregular pulse to the patient and obtaining an electrocardiogram for determining atrial fibrillation. Initially, a pulse is detected at regular time intervals of a first appendage of the patient when motionless using a pulse detector secured to the first appendage and pulse rhythms from a succession of time intervals are detected each corresponding to a respective interval of time between successive pulse beats of a sequence of the pulse beats. Then, an electrically conductive unit is attached to a second appendage of the patient, or a wearable electrocardiogram is attached to the patient, and electrocardiograms signals are detected simultaneously with pulse rhythms while the first appendage is motionless and analyzed to determine whether, in combination, they are indicative of atrial fibrillation. If so, an indication of atrial fibrillation is provided at least to the patient.

25 Claims, 4 Drawing Sheets

(56) References Cited

U.S. PATENT DOCUMENTS

| | | |
|---|---|---|
| 4,621,643 A | 11/1989 | New, Jr. et al. |
| 5,113,869 A | 5/1992 | Nappholz et al. |
| 5,117,834 A | 6/1992 | Kroll et al. |
| 5,228,449 A | 7/1993 | Christ et al. |
| 5,342,404 A | 8/1994 | Alt et al. |
| 5,456,261 A | 10/1995 | Luczyk |
| 5,471,991 A | 12/1995 | Shinnar |
| 5,609,158 A | 3/1997 | Chan |
| 5,626,143 A | 5/1997 | Meyer, III |
| 5,772,604 A | 6/1998 | Langberg et al. |
| 5,842,997 A | 12/1998 | Verrier et al. |
| 5,941,831 A | 8/1999 | Turcott |
| 6,095,984 A | 8/2000 | Amano et al. |
| 6,126,595 A | 10/2000 | Amano et al. |
| 6,249,700 B1 | 6/2001 | Alt |
| 6,327,499 B1 | 12/2001 | Alt |
| 6,519,490 B1 * | 2/2003 | Wiesel ............... A61B 5/046 600/518 |
| 7,072,709 B2 * | 7/2006 | Xue ............... A61B 5/0452 600/509 |
| 7,680,532 B2 | 3/2010 | Wiesel |
| 7,706,868 B2 | 4/2010 | Wiesel |
| 2007/0276270 A1 * | 11/2007 | Tran ............... A61B 5/0022 600/508 |
| 2008/0103402 A1 * | 5/2008 | Stickney ............... A61B 5/0402 600/509 |
| 2012/0232416 A1 * | 9/2012 | Gilham ............... A61B 5/7246 600/515 |
| 2012/0265086 A1 * | 10/2012 | Lux ............... A61B 5/046 600/515 |

OTHER PUBLICATIONS

Braunwald's A Textbook of Cardiovascular Medicine, 7th Edition, 2004, pp. 817, 840.

Degown's Diagnostic Examination, 8th Edition, 2004, p. 362.

Joseph Wiesel et al "The Use of a Modified Sphygmomanometer to Detect Atrial Fibrillation in Outpatients", PACE, vol. 27 (May 2004).

Braunwald's A Textbook of Cardiovascular Medicine, 7th Edition, 2005, pp. 817, 840.

* cited by examiner

METHOD AND APPARATUS FOR DETECTING ATRIAL FIBRILLATION

CROSS-REFERENCE TO RELATED APPLICATION

This application claims priority of U.S. provisional patent application Ser. No. 61/871,906 filed Aug. 30, 2013, incorporated by reference herein.

BACKGROUND OF THE INVENTION

1. Field of the Invention

The present invention generally relates to a method of and an apparatus for detecting atrial fibrillation.

2. Discussion of the Related Art

The heart is the major muscle that functions as the primary pump for blood flow throughout the body. The heart contains two upper chambers called atria and two lower chambers called ventricles. The right atrium receives oxygen-depleted blood while the left atrium receives blood enriched with oxygen from the lungs. When the atria are full, the outlet valves within the heart open and the atria squeeze blood into the ventricles. The right ventricle then pumps oxygen-depleted blood to the lungs while the left ventricle pumps oxygen-enriched blood to all parts of the body. In this fashion, the heart functions primarily as a double sided pump.

The heart's internal pacemaker, known as the sinus node, signals the start of each heart beat. This signal originates in the right atrium in the sinoatrial node and travels simultaneously to the left atrium and down to the interatrial septum to the atrioventricular node. This electrical impulse results in a "p" wave on the electrocardiogram. This cycle of electrical stimulation that occurs normally is referred to as normal sinus rhythm. The contraction of the ventricles is preceded by QRS waves on the electrocardiogram (ECG), which is the electrical activity that begins ventricular contraction. This electrical activity is also often referred to as the "R" wave. The contraction of the heart occurs after the R wave. The impulse caused by cardiac contractility is transmitted through the arteries and is detected as a pulse. This pulse beat usually occurs from about 200 msec to about 700 msec after the R wave.

Many rhythm abnormalities may cause an irregular heart rhythm. Atrial fibrillation is a rhythm abnormality in which the atria do not contract normally. Instead, there is a continuously varying pattern of electrical activation of the atria resulting in a rapid highly irregular pattern of impulses reaching the atrioventricular node. The atrioventricular node acts as a filter and allows a reduced number of these impulses to reach the ventricles which results in a highly irregular heartbeat pattern. Since there is no organized electrical activity in the atrium, atrial fibrillation does not produce a p wave on the ECG.

Atrial fibrillation is one of the most common arrhythmias requiring medical attention. Atrial fibrillation may be caused by a number of heart conditions, such as coronary artery disease, myocardial infarction, heart valve abnormalities, and high blood pressure. These conditions may stretch or scar the atria, thereby causing irregularities in the heart system. Atrial fibrillation may also accompany lung problems or thyroid gland disorders and is also associated with significant morbidity and possible mortality. All persons, young and old, female or male, including the visually and/or sight impaired, may experience atrial fibrillation.

The most serious complication of atrial fibrillation is formation of a blood clot in the left atrium which may result in a stroke. The standard therapy used to prevent strokes in patients with risk factors for a stroke and atrial fibrillation is an anticoagulant, or blood thinner. Many people who develop atrial fibrillation, however, are unaware of their abnormal rhythm.

Recommendations have been made for people at risk of developing atrial fibrillation, to check their pulse periodically. Checking the pulse manually by palpation is often difficult for some people, especially the elderly, to do reliably. Therefore, use of a device that periodically automatically assess the heart rhythm and alerts the patient to the presence of atrial fibrillation would be helpful in getting patients with atrial fibrillation to be treated earlier. This may help prevent strokes in patients who are unaware that they have atrial fibrillation.

There are devices available that can be used by patients to screen for atrial fibrillation. The electrocardiogram (ECG) is the gold standard for determining if a person has atrial fibrillation. However, checking the ECG is cumbersome because it requires the person to place at least two electrodes on different body locations, such as both arms, an arm and a leg or an arm and the chest, or two locations on the chest. Also ECG monitoring at home often requires a technician and then a physician to read the ECG. The cost of this approach is prohibitive for the general population at risk of atrial fibrillation.

There are devices that can read the ECG automatically. However, they are easily compromised by a noisy signal, which is very common with ECG's. A noisy ECG signal can result in what is described as artifacts on the ECG signal. These artifacts can appear to be multiple R waves in an irregular pattern. These artifactual R waves will not have p waves preceding them and will, thus, result in the ECG meeting the criteria for diagnosing atrial fibrillation even though the true rhythm may be regular.

The use of blood pressure monitors and smartphones which can determine the time interval between pulse beats have been described. The blood pressure monitors rely on plethysmographic signals to detect the pulse, while smartphones can use the light transmittance through the skin to detect the pulse. The blood pressure devices, in particular, are able to detect the pulse reliably with artifacts rarely affecting the pulse signal. These modalities rely on assessing the regularity of the pulse rhythm which is irregular in atrial fibrillation. However, other rhythm abnormalities, such as extra heart beats may cause an irregular heart rhythm. These extra beats often follow normal beats that have both p and R waves on the ECG. Differentiating the rhythms due to extra heartbeats from atrial fibrillation can be performed most accurately by using the ECG.

Combining both the ECG recording and the pulse recording can improve the accuracy of detecting the true pulse beats. As mentioned previously, noise in either the ECG or pulse rhythm recording can result in artifacts that look like extra beats. Heart beats that occur with an adequate time interval following the previous beat to generate a pulse will always generate an R wave on the ECG and a pulse beat. Therefore, it is possible to use the pulse rhythm recording to help determine if what looks like an R wave on the ECG is due to a very premature R wave or an artifact since that electrical activity will not have a pulse beat. By deleting that electrical activity from the ECG, it is possible to generate a modified ECG that will have less electrical noise and very premature beats. This new modified ECG recording can then be analyzed for regularity. If it is regular, then the rhythm is not atrial fibrillation. If it is irregular, then the R waves on the modified ECG can be identified, and an attempt can be made to detect the preceding p waves. If the p waves are present, then the rhythm is not atrial fibrillation. If the p waves are absent, then the rhythm is atrial fibrillation.

The ECG recording and the pulse rhythm recording can be most easily compared by shifting the time of the ECG by from about 200 msec to about 700 msec so that the R waves occur at a later time. When the ECG time is shifted enough to account for the delay in generating the pulse rhythm, then the ECG and pulse recordings should have R waves and pulse beats occurring simultaneously. That is the time shift that can be used to generate the new modified ECG recording.

What is needed is a device that can be worn on a daily basis and can periodically take automatic pulse readings when the person is not moving so as to accurately determine if the heart rhythm is irregular.

What is further needed is for that device to inform the person when the automatic pulse reading showed an irregular rhythm and a combined ECG and pulse rhythm recording needs to be taken.

What is further needed is for the combined pulse and ECG recording to be analyzed to determine if atrial fibrillation is present and to inform the person of that result.

Methods for determining if an ECG waveform is noisy has been described in U.S. Pat. No. 8,639,316. However, in this patent publication, the presence of noise is determined by analyzing the properties of the ECG signal such as the morphology, amplitude or frequency content of the signal. This can also be applied to other physiological signals such as blood pressure waveforms. However, there is no mention of using a combination of physiological signals to determine if the ECG signal is noisy. There is also no mention of generating a new ECG recording by using a physiological signal to modify the ECG signal and then using that modified ECG to determine if atrial fibrillation is present.

U.S. Pat. Appln. Publ. No. 20130060154 describes a watch-like device that is worn on the wrist and can detect pulse signals which can be used to determine if atrial fibrillation is present. However, it does not describe obtaining recordings periodically and automatically when the person is not moving.

BRIEF SUMMARY OF THE INVENTION

The present invention provides a method and apparatus that can screen for atrial fibrillation periodically by automatically checking for a pulse irregularity when the appendage, on which the apparatus is worn or secured, is motionless. It then adds an additional step to determine if atrial fibrillation is present when the pulse rhythm is found to be irregular, by taking a combined ECG and pulse reading. In this combined reading, the presence of atrial fibrillation may be determined by (i) detecting the pulse beat intervals and the ECG signal simultaneously when at least one appendage is motionless, (ii) generating a new modified ECG recording that includes only heartbeats that are present on both the ECG and pulse rhythm recording, (iii) analyzing the modified ECG recording for regularity or irregularity, (iv) if an irregularity is found, then determining if "p" waves are present preceding the R waves on the modified ECG, (v) determining if atrial fibrillation is present by the lack of p waves, and (vi) communicating this information to the user so that a medical practitioner may be consulted by the user for further testing and/or treatment.

The present invention also provides a method of and an apparatus for detecting irregular pulses and ECG rhythms during a time period and storing this information for comparison with the pulse rhythm at later time periods. The present invention may also detect patterns over multiple time periods and compare the patterns over various time periods.

Pulse beats may be obtained by plethysmography such as the use of an inflatable cuff wrapped around a person's appendage, such as a wrist, which detects the pulse beats by either oscillometric or auscultatory means. The time intervals between pulse beats can be determined during cuff deflation or while the cuff is inflated at a fixed pressure. This cuff device can be incorporated into a wrist watch that can be worn on a daily basis and automatic recordings obtained periodically, such as once a day or once a week. The device would inflate the cuff only when the wrist has been stationary and motionless for a specified time period before the inflation as determined by an accelerometer within the device. The waveform generated by the device would only be analyzed if the accelerometer confirmed that no movement occurred during the measurement period.

Pulse beats may also be monitored through changes in light transmitted through various body appendages. Each pulse beat changes the light transmission through a location on the appendage. The change in the light transmission corresponds to a pulse beat and the time intervals between pulse beats may be determined. This can be done with a wrist watch device that includes a light source and a light sensor on the part of the wrist watch that makes contact with the skin at the wrist. This wrist watch that can be worn on a daily basis and automatic recordings can be obtained periodically, such as once a day or once a week. The device measures light transmittance only when the wrist has been stationary and motionless for a specified time period before the measurement as determined by an accelerometer within the device. The waveform generated by the device would only be analyzed if the accelerometer confirmed that no movement occurred during the measurement period.

Pulse beats may also be monitored using other plethysmographic devices, ultrasound devices that measure arterial motion with each pulse beat, ultrasound doppler devices that detect blood flow within an artery or devices that rely on localized compression of the artery to detect the presence of a pulse beat. Using any of these techniques the time intervals between pulse beats can be determined.

ECG signals may be obtained by placing electrical conducting leads on the limbs, other appendages or the chest. It may also be obtained by obtaining electrical signals from conducting leads in the heart or in other locations in the chest such as in pacemakers.

A monitoring method of the present invention includes communicating this information to a user such as via a screen display, a paper printout, a tone, or auditory, vibratory or other sensory communication.

The invention may utilize algorithmic or heuristic techniques to determine whether the ECG and pulse beats signal the possible presence of atrial fibrillation.

Other features and advantages of the present invention will become apparent from the following detailed description of the invention with reference to the accompanying drawings.

BRIEF DESCRIPTION OF THE DRAWINGS

For a better understanding of the present invention, reference is made to the following description and accompanying drawings, while the scope of the invention is set forth in the appended claims:

DETAILED DESCRIPTION OF THE INVENTION

Figure 1:
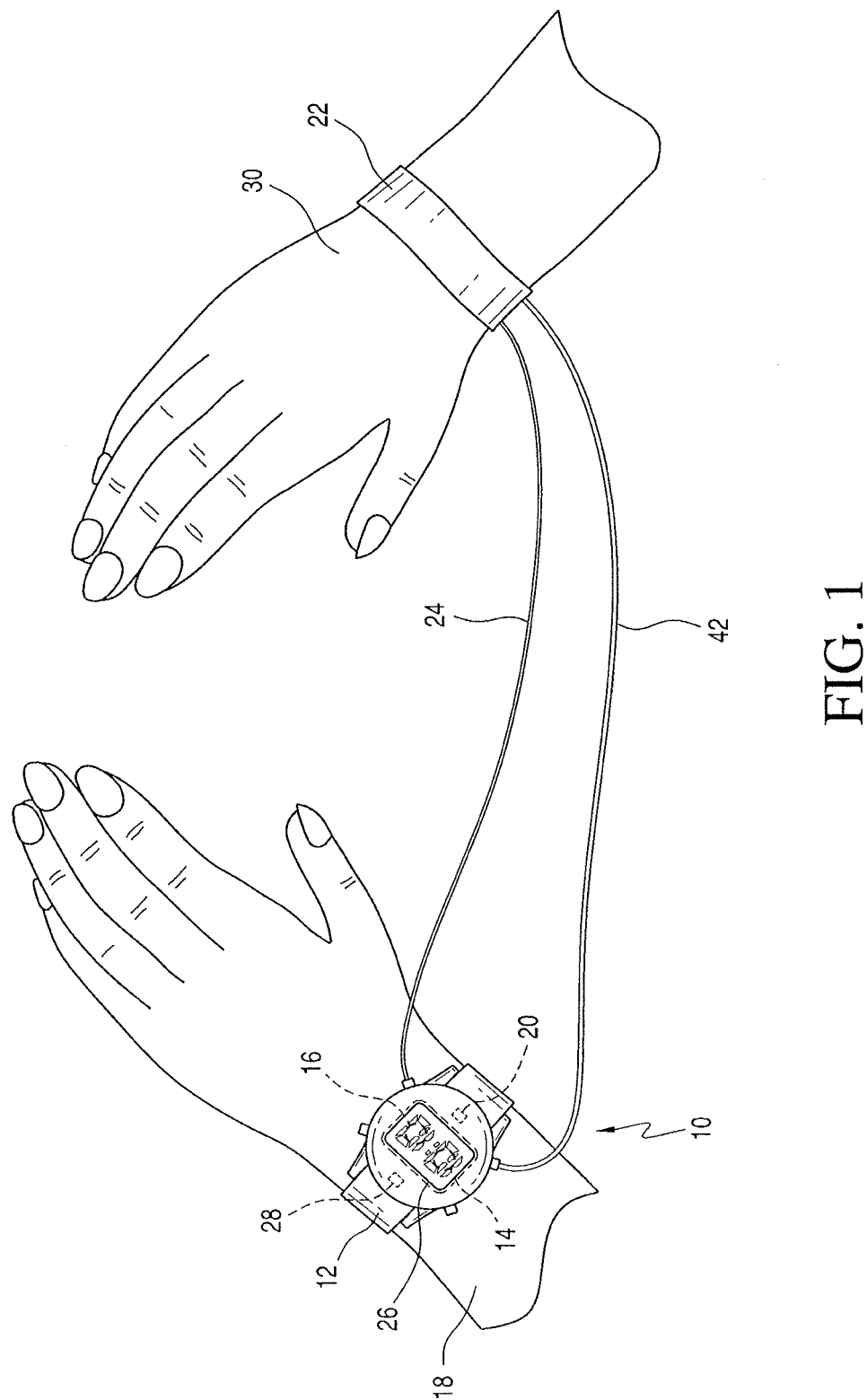
FIG. 1 is shows an exemplifying, non-limiting embodiment of a wrist watch in accordance with the invention.

Referring to the accompanying drawings wherein like reference numbers refer to the same or similar elements, one embodiment of the apparatus in accordance with the invention and that may be used in a method in accordance with the invention uses pulse beats and an ECG that are detected using a wristwatch 10 which has a conductive watch band or strap 12 as shown in FIG. 1. The watch band or strap 12 is an example of a securing mechanism for securing a housing 40 including the electrical and mechanical components of the invention to the wrist of the patient. Other securing mechanisms may be used in the invention.

The wrist watch 10 also includes a light source 14 and sensor 16 on the bottom side of watch 10, preferably directly on or against the skin surface 18. The light source 14 and light sensor 16 are controlled to transmit light to the skin of the wearer and receive reflected light which can be converted into a pulse in a manner known to those skilled in the art to which this invention pertains. Other pulse detector mechanisms may also be used in the invention and included in the housing of the watch 10 that is secured to the wrist of the wearer, or another appendage of the wearer.

An accelerometer 20 is preferably built into the housing 40 of the watch 10. The ECG is obtained from electrically conductive portions in wrist straps 12, 22 on and in skin contact with both wrists of the same person with a limb lead 24 from strap 22 connected to the housing 40 of the watch 10. Data from the accelerometer 20 is used to determine whether the wrist to which the watch 10 is secured is sufficiently motionless or moving. In this context, motionless means that the position of the wrist is not changing. A totally still state of the appendage is desirable but practically difficult to achieve. Therefore, a threshold may be set as to the degree of permissible motion of the appendage and an indication of motion below the threshold may be considered a motionless state.

Since the light source 14 and sensor 16 are operative on the underside of the watch 10, and hence in dotted lines in FIG. 1, the wrist watch 10 would be able to keep track of time via a conventional time keeping and displaying mechanism 26 visible to the wearer and determine when the next automated pulse reading should be obtained. A timing mechanism to achieve this timed determination is readily configured to one skilled in the art in view of the disclosure herein. For example, pulse readings may be obtained once a day to detect if the patient has an episode of atrial fibrillation. The wrist watch 10 would automatically begin to determine if the wrist is moving when the time for the next pulse reading occurs. This movement detection is preferably performed using the accelerometer 20, but as an alternative, another movement detection means or mechanism may be used in the invention.

If the accelerometer 20 determines that the wrist is moving at that time, it will not attempt to take a pulse reading. The accelerometer 20 may be used to check for movement again a set period of time later, e.g., five minutes later, and continue to enable such movement checking until it is found that the wrist is motionless. At that time, a 30 second pulse rhythm will be obtained. If data from the accelerometer 20 confirms that no movement occurred during that 30 second reading, then the pulse rhythm obtained during the 30 second period will be analyzed to determine if the pulse rhythm is regular or irregular. If it is regular, then atrial fibrillation is not present and the watch 10 will obtain the next reading according to its programmed schedule, e.g., the following day at the same set time.

If the pulse rhythm is irregular, the watch 10 will signal the person wearing the watch 10 by voice, beeping, vibration, a text, a light or on the watch screen display 26, that an abnormal rhythm was found and an ECG needs to be taken. The mechanism that provides this is referred to as a signaling mechanism 28 and may be incorporated into the housing 40 of the watch 10. The signaling mechanism 28 may be configured to perform one or more of these actions or responses to the determination of the irregularity of the pulse rhythm by the processor 32 in the housing 40 of the watch 10 (see FIG. 2).

Once notified that an ECG needs to be taken, the person should then take a conductive wrist strap 22 that is incorporated in the wristwatch band 12 and pull it off the watch band 12 and place it on the other wrist (as shown in FIG. 1). The wrist strap 22 will have a wire or lead 24 that is in place connecting it to the housing of the watch 10, i.e., to the electronic componentry in the housing of the watch 10 (schematically shown in FIG. 2). A connector 42, e.g., an elastic cord, is optionally provided to connect the wrist strap 40 to the housing 40. Once the second wrist strap 22 is in place, the conductive wristwatch band 12 and the other wrist strap 22 become two leads for the ECG. The wristwatch band 12 is positioned to have continuous contact with the skin surface 20 on the wrist and the watch 10, i.e., processor 32 therein, can detect that the second wrist strap 22 has made contact with the skin surface 30 since an ECG signal will then be generated.

At that point, data from the accelerometer 20 will be used to determine if the wrist watch 10 is motionless. If it is not, then the wrist watch 10 will signal to the person to stop moving both arms and to relax. If data from the accelerometer 20 provides a determination that there is no movement, then the ECG and the pulse rhythm will be recorded simultaneously for 30 seconds. This recording may be stored in a memory 34 of the housing of the watch 10 (see FIG. 2).

Figure 2:
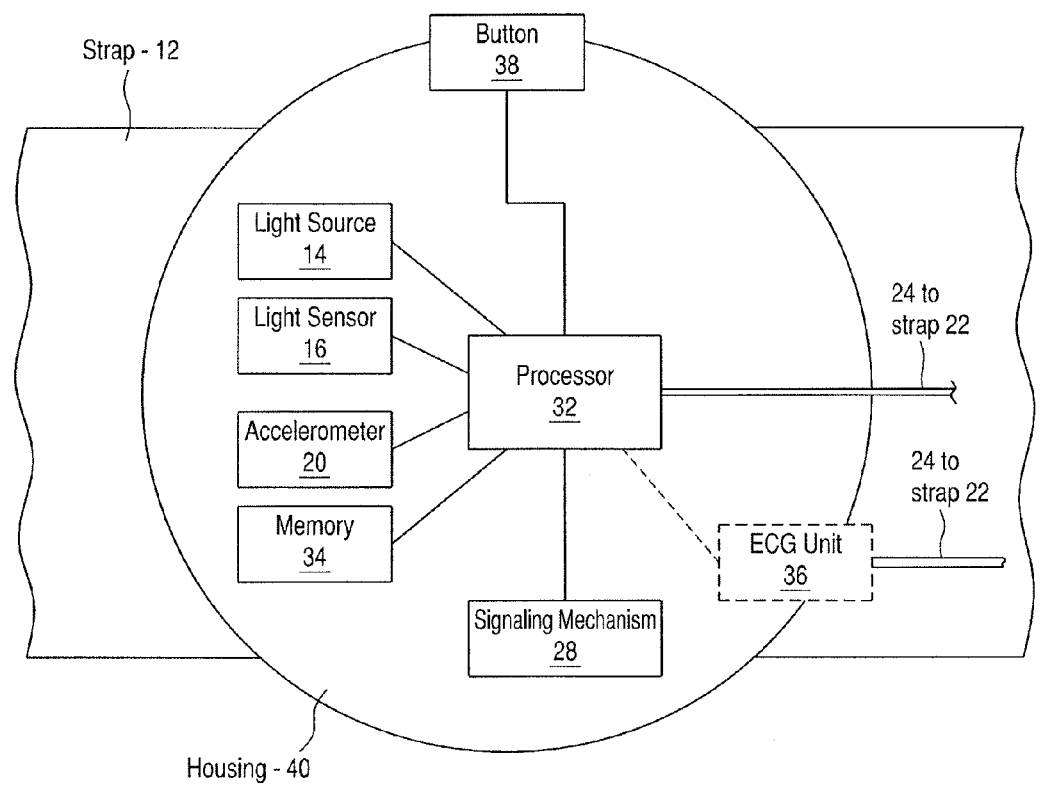
FIG. 2 is a schematic showing the components in the housing of the wrist watch in accordance with the invention.

Once the ECG and pulse signals are obtained, the processor 32 in the wristwatch 10 will analyze the two signals (see FIG. 2). The pulse rhythm recording will be used to help the processor 32 determine if what looks like an R wave on the ECG is due to a very premature R wave or an artifact. Electrical activity on the ECG that does not have a pulse beat associated with it will be deleted (through processing performed by the processor 32 upon execution of appropriate software being executed by the processor 32). By deleting that electrical activity from the ECG, the processor 32 is configured to generate a modified ECG that will have less electrical noise and very premature beats.

This new modified ECG recording can then be analyzed by the processor 32 for regularity using algorithms or other processing techniques. If it is regular, then the rhythm is not atrial fibrillation and the person will be informed by voice, by a green light or by the watch screen that the rhythm is normal, via the signaling mechanism 28, and the next automatic reading will be performed as scheduled. If it is irregular, then the R waves on the modified ECG can be identified by the processor 32, and an attempt can be made to detect the preceding p waves. If the p waves are present, then the rhythm is not atrial fibrillation and the person will be informed that the rhythm is normal, again by means of the signaling mechanism 28. If the p waves are absent, then the rhythm is atrial fibrillation and the person will be informed that he has atrial fibrillation via the signaling mechanism 28 and should seek the advice of a physician. After the person acknowledges that he has received this message by pressing a button 38 on the watch 10, then the watch 10 will take the next reading as scheduled. If no acknowledgement is made, then the watch 10 will continue to show that atrial fibrillation was detected.

The processor 32 can store the time of each pulse beat, the intervals between pulse beats and other information in the memory 34 (see FIG. 2). The memory 34 may include RAM or other device memory or include a hard disc, a floppy disk or other memory devices. The processor 32 may comprise a microprocessor, and applications specific integrated circuit (ASIC), a programmable logic array (FLA) or reduced instruction set chip (RISC).

Instead of incorporating the ECG determination and analysis unit in the processor 32, the ECG device may be a separate ECG recorder with a signal output that can be connected to the wrist watch processor 32 (see ECG device 36 in dotted lines in FIG. 2). The wrist watch 10 may also have one lead incorporated into other accessories on the device such that it can be strapped onto the limbs or chest of the patient. The ECG device 36 may thus be a wearable electrocardiogram device configured to be attached to the limbs or the chest of the patient and provides an electrocardiogram signal to the processor 32 via an electrical lead (in dotted lines in FIG. 2).

Figure 5:
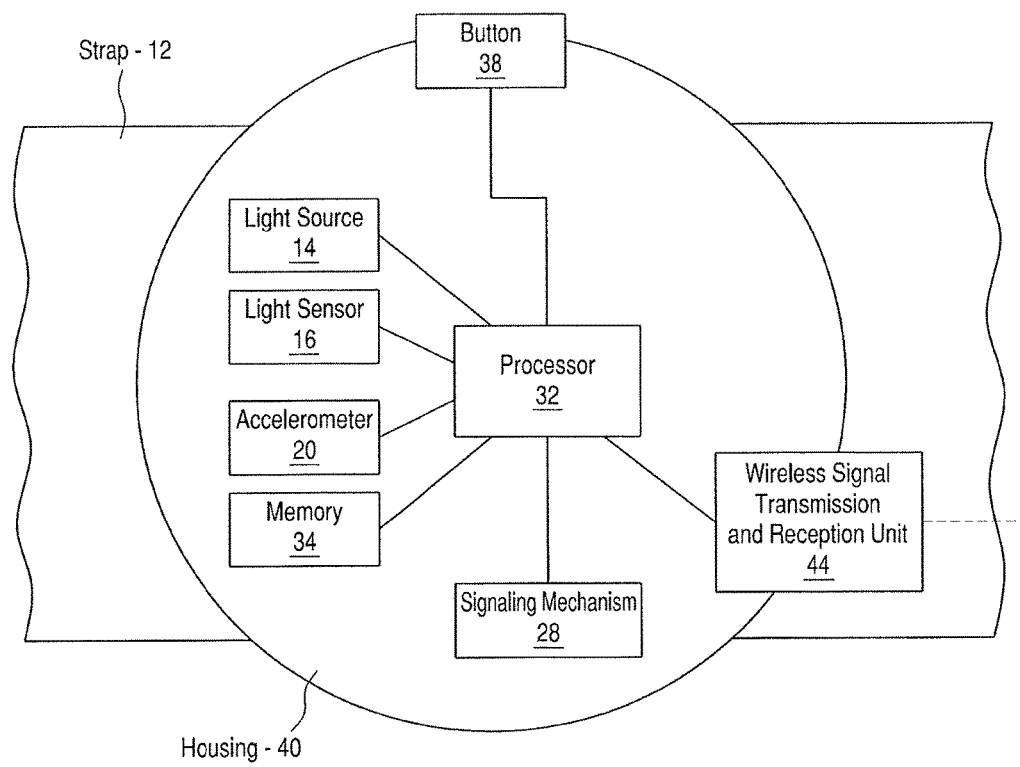
FIG. 5 is a schematic similar to FIG. 2 but including a wireless ECG device.
Figure 5:
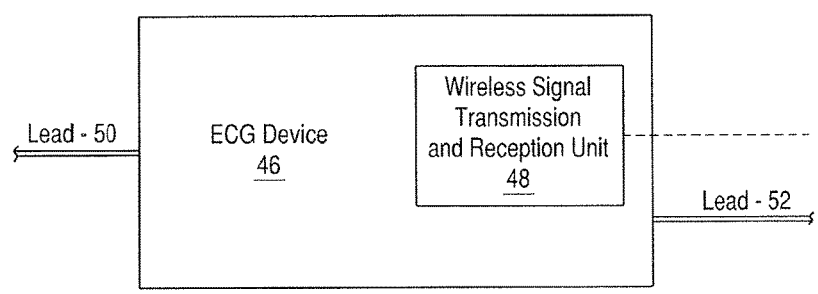

Referring now to FIG. 5, the wrist watch 10 may also communicate wirelessly with a separate ECG device 46 that may have leads 50, 52 placed upon the person's limbs or chest or is worn by the person. The wireless communication may be with radio waves using Bluetooth, near field communication technology or other data communication technologies. One embodiment using wireless technology would include the ECG device 46 that is separate and apart from the housing 40 of the wrist watch 10, and which would incorporate a wireless signal transmission and/or reception unit 48, and two or more electrically conductive leads 50, 52 that are adapted to be secured or otherwise attached at a respective location to the person for which the ECG is to be taken, specifically in contact with skin of the person. The ECG device 46 may thus be configured as a wearable electrocardiogram device attachable to the limbs or chest of the patient with the leads 50, 52 extending therefrom to be positioned in contact with skin of the patient. The housing 40 of the wrist watch 10 is then also provided with a wireless signal transmission and/or reception unit 44 and configured to issue commands to be wirelessly transmitted to the ECG device 46 to cause the ECG device 46 to obtain an electrocardiogram signal via the leads 50, 52 and output an ECG which is then transmitted to the wrist watch 10 via the wireless signal transmission and/or reception units 44, 48. An example of a wearable electrocardiogram device 36 that may be used in the invention is a T-shirt manufactured by HealthWatch of Tel Aviv, Israel.

In either case, the processor 32 determines from the pulse beats and ECG if the results suggest atrial fibrillation or not. Programming of the processor 32 to perform this determination is readily ascertainable by those skilled in the art in view of the disclosure herein. The processor 32 can then deliver the results to a printer, a display, a vibration generator, and/or an auditory generator, etc. (signaling mechanism 28) which may include an indication that the pulse beat pattern is regular, irregular, in possible atrial fibrillation, or that a physician should be contacted. Other information, such as the pulse rate, may also be displayed.

Figure 3:
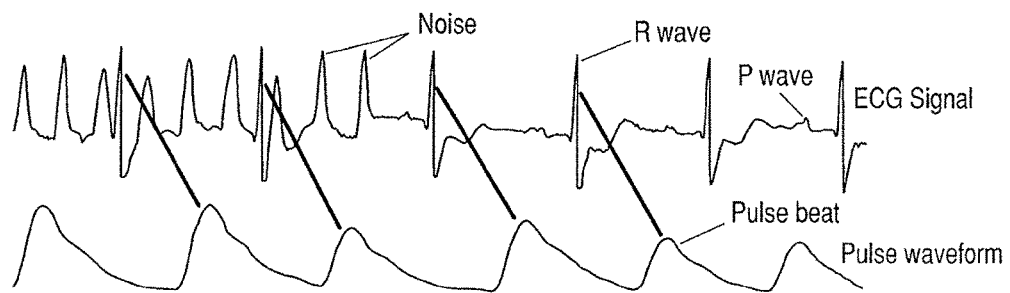
FIG. 3 is an example of an ECG signal with noise and a simultaneous pulse beat waveform obtained from a pulse oxymeter.

FIG. 3 shows an exemplifying ECG signal, the top signal, simultaneous with a pulse waveform, the bottom signal. The diagonal lines extending between the ECG signal and the pulse waveform show the R wave with the resulting pulse beat generated by the cardiac contraction caused by the R wave. ECG waveforms that do not have a resulting pulse beat are due to electrical noise. The noise stops after the third R wave. In this example of a recording, the ECG signal shows noise artifact that cannot easily be differentiated from the real R waves.

Figure 4:
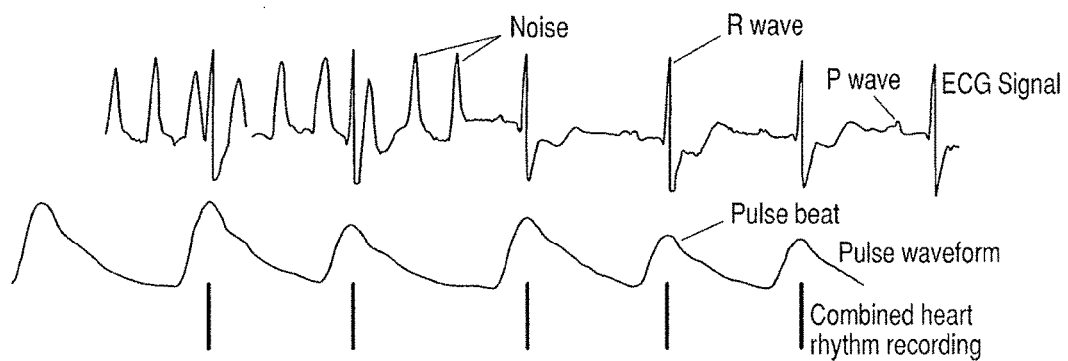
FIG. 4 shows the ECG time shifted so that the R waves coincide with the pulse beats and location of the R waves that would not be deleted from the new modified ECG.

FIG. 4 shows an exemplifying ECG signal, the top signal, time shifted so that pulse beats, the middle signal, coincide with R waves. The noise artifact on the ECG signal can then be ignored since they do not coincide with the pulse beats. Combined heart rhythm recording, the lower signal, shows which wave would not be deleted from the new modified ECG generated by the processor 32 in the manner described above, i.e., the new ECG recording can be generated at each time point where both R wave and pulse beats occur simultaneously. If this heart rhythm recording were regular, then the rhythm would be determined not to be atrial fibrillation. However, since this heart rhythm recording is irregular, further analysis of the modified ECG is needed to determine the presence or absence of p waves. The R waves are analyzed by the processor 32 to determine if there are p waves that preceded them. Since p waves are noted before the R waves on this tracing, the rhythm would be called not atrial fibrillation.

Advantageously, the invention provides a method and apparatus that easily detect the presence of atrial fibrillation, and differentiates atrial fibrillation from non-atrial fibrillation rhythms including normal and other abnormal rhythms.

A still further advantage is that the invention provides relatively simple, non-invasive monitoring for long term at home or other location outside of a physician's office. Nevertheless, the use of the invention may occur at a physician's office or hospital or at any location where long term heart monitoring is desired.

Additional information about heart monitoring and processing of heart signals is disclosed in U.S. Pat. Nos. 6,519,490, 7,020,514, 7,680,532 and 7,706,868, to the same inventor. The disclosures of all of these patents are incorporated by reference herein. Also, the techniques disclosed in these patents may be used in combination with or as modifications to the techniques disclosed herein, and such are also considered to be inventions Although the present invention has been described in relation to particular embodiments thereof, many other variations and modifications and other uses may become apparent to those skilled in the art. It is preferred, therefore, that the present invention be limited not by this specific disclosure herein, but only by the appended claims.

What is claimed is:
1. A method of determining atrial fibrillation, comprising:
   performing a first stage of analysis to determining if pulse beats form an irregular pattern, the first stage comprising:

detecting a pulse of a first appendage of a patient by means of a pulse detector secured to the first appendage;

detecting pulse rhythms from a succession of time intervals each corresponding to a respective interval of time between successive pulse beats of a sequence of the pulse beats; and determining, using a processor, whether the pulse beats form an irregular pattern; and only when it is determined in the first stage that the pulse beats form an irregular pattern, indicating the presence of an irregular pulse and performing a second stage in which an electrocardiogram is obtained for determining atrial fibrillation, the second stage comprising:

detecting electrocardiogram signals simultaneously with pulse rhythms;

analyzing, using a processor, the detected pulse beats and electrocardiogram signal to determine whether, in combination, they are indicative of atrial fibrillation;

time shifting the electrocardiogram signal to generate a modified electrocardiogram signal, such that electrical activity which results in ventricular contraction occurs at a later time, said later time coinciding with pulse beats generated by the ventricular contraction; and providing an indication of atrial fibrillation, when present.

2. The method of claim 1, further comprising, in the second stage, securing an electrical conductor in contact with skin of a second appendage of the patient; and determining that the first appendage is motionless by means of a motion detector secured to the first appendage;

the electrocardiogram signals being detected simultaneously with pulse rhythms only after it is determined that the first appendage is motionless.

3. The method of claim 2, further comprising, in the second stage, determining that the first appendage is not motionless by means of the motion detector secured to the first appendage; and providing an indication to the patient to place the first appendage in a motionless state when it is determined that the first appendage is not motionless.

4. The method of claim 2, further comprising, in the second stage, determining whether the first appendage is motionless during the detection of the electrocardiogram signals simultaneously with pulse rhythm; and when it is determined that the first appendage is not motionless during the detection of the electrocardiogram signals simultaneously with pulse rhythm, providing an indication to the patient to place and maintain the first appendage in a motionless state for the duration of the detection of the electrocardiogram signals simultaneously with pulse rhythm.

5. The method of claim 2, wherein the motion detector comprises an accelerometer that measures acceleration of the first appendage.

6. The method of claim 1, wherein the step of detecting electrocardiogram signals comprises obtaining an electrocardiogram signal via an electrical lead from a wearable electrocardiogram configured to be attached to the limbs or the chest of the patient.

7. The method of claim 1, wherein the step of detecting electrocardiogram signals comprises:

attaching a wearable electrocardiogram attached to the limbs or the chest of the patient; and transmitting, via radio waves, the electrocardiogram signal from the wearable electrocardiogram to a housing of the processor.

8. The method of claim 1, wherein the pulse detector comprises a light transmitter and light sensor, the method further comprising positioning the light transmitter to transmit light against skin of the patient and the light sensor to receive tight reflected from the skin of the patient.

9. The method of claim 1, further comprising periodically determining whether the first appendage used to detect the pulse is motionless by means of a motion detector secured to the first appendage and detecting pulse rhythms from a succession of time intervals only after it is determined that the first appendage is motionless and while the first appendance is motionless.

10. The method of claim 9, further comprising, in the first stage, providing an indication to the patient to place the first appendage in a motionless state when it is determined that the first appendage is not motionless;

determining whether the first appendage is motionless during the succession of time intervals; and when it is determined that the first appendage is not motionless during the succession of time intervals, providing an indication to the patient to place and maintain the first appendage in a motionless state for the duration of the succession of time intervals.

11. The method of claim 9, further comprising performing the step of detecting a pulse of a first appendage of a patient by means of a pulse detector secured to the first appendage automatically and periodically.

12. The method of claim 9, further comprising, in the second stage, securing an electrical conductor in contact with skin of a second appendage of the patient; and determining that the first appendage is motionless;

the electrocardiogram signals being detected simultaneously with pulse rhythms only after it is determined that the first appendage is motionless.

13. The method of claim 1, further comprising performing the step of detecting a pulse of a first appendage of a patient by means of a pulse detector secured to the first appendage automatically and periodically.

14. The method of claim 1 wherein the pulse detector is integrated into a wristwatch.

15. The method of claim 1, wherein determining whether the pulse beats form an irregular pattern further comprises adjusting the determination to account for a previous irregular pattern that was found to be not atrial fibrillation by a previous second stage combined detection of pulse beats and electrocardiogram signal.

16. The method of claim 15, wherein adjusting the determination of an irregular pattern further comprises:

storing said previous irregular pattern as a historical non-atrial fibrillation pattern and comparing each new irregular pattern to said historical non-atrial fibrillation pattern and not performing the second stage if said pattern matches said historical non-atrial fibrillation pattern.

17. The method of claim 15, wherein adjusting the determination of an irregular pattern comprises increasing a threshold for pulse rates used in the determination of an irregular pattern.

18. The method of claim 15, wherein adjusting the determination of an irregular pattern further comprises:
increasing a threshold that is indicative of irregularity if exceeded by the quotient formed by dividing standard deviation of time intervals by mean of time intervals corresponding to a heartbeat.

19. The method of claim 17, wherein the threshold value is increased by beats per minute when it is not determined that the detected pulse beats and electrocardiogram signal in combination, are indicative of atrial fibrillation.

20. The method of claim 1, wherein the magnitude of the time shift is from about 200 to about to 700 msec.

21. The method of claim 1, wherein the step of analyzing the detected pulse beats and electrocardiogram signal to determine whether, in combination, they are indicative of atrial fibrillation further comprises deleting, on the modified ECG signal, R waves that occur without simultaneous pulse beat.

22. The method of claim 1, further comprising forming the modified ECG signal to include only the R waves that occur on the time shifted electrocardiogram and have a simultaneous pulse beat recording.

23. The method of claim 22, wherein the step of analyzing the detected pulse beats and electrocardiogram signal to determine whether, in combination, they are indicative of atrial fibrillation further comprises analyzing the modified ECG signal to determine whether it is regular and not atrial fibrillation or irregular and indicative of possible atrial fibrillation.

24. The method of claim 23, wherein the step of analyzing the detected pulse beats and electrocardiogram signal to determine whether, in combination, they are indicative of atrial fibrillation further comprises analyzing the modified ECG signal to determine presence of organized electrical activity due to atrial depolarization ("p" wave) occurring just prior to the selected R waves.

25. The method of claim 24, wherein the step of analyzing the detected pulse beats and electrocardiogram signal to determine whether, in combination, they are indicative of atrial fibrillation further comprises further comprising analyzing the modified ECG signal for the presence of "p" waves that determine the rhythm not to be indicative of atrial fibrillation and the absence of "p" waves determine the rhythm to be atrial fibrillation.

* * * * *